United States Patent [19]

Dennehey et al.

[11] 4,340,052
[45] Jul. 20, 1982

[54] CONNECTION SITE PROTECTOR

[75] Inventors: T. Michael Dennehey, Arlington Heights; Richard J. Greff, Ingleside; Ludwig Wolf, Jr., Crystal Lake, all of Ill.

[73] Assignee: Baxter Travenol Laboratories, Inc., Deerfield, Ill.

[21] Appl. No.: 194,733

[22] Filed: Oct. 7, 1980

[51] Int. Cl.³ .............................................. A61M 3/00
[52] U.S. Cl. .................................................... 128/247
[58] Field of Search ............... 128/247, 214 R, 214 G, 128/215; 285/DIG. 2, 260

[56] References Cited

U.S. PATENT DOCUMENTS 2,857,912 10/1958 Feinstone et al. .................. 128/215
3,456,965 7/1969 Gajewski et al. .
4,043,333 8/1977 Munsch ........................... 128/214 R

OTHER PUBLICATIONS

Proceedings of an International Symposium at Paris, Nov. 2, 3, 1979, "Continuous Ambulatory Peritoneal Dialysis", Excerpta Medica 1980.

Primary Examiner—John D. Yasko
Attorney, Agent, or Firm—Paul C. Flattery; Garrettson Ellis; Geroge H. Gerstman

[57] ABSTRACT

A contamination protector for a medical device, principally for use in surrounding and protecting a connection between a plastic dialysis solution container (10) and tubing (22) carried by a patient practicing continuous ambulatory peritoneal dialysis. The protector is generally cylindrical in shape, and opens and closes much like a "clamshell." The inner wall surface (34) of the protector is adapted to carry a material (36) which holds a sterilizing agent in contact with a medical connection when the protector is in the closed position.

2 Claims, 7 Drawing Figures

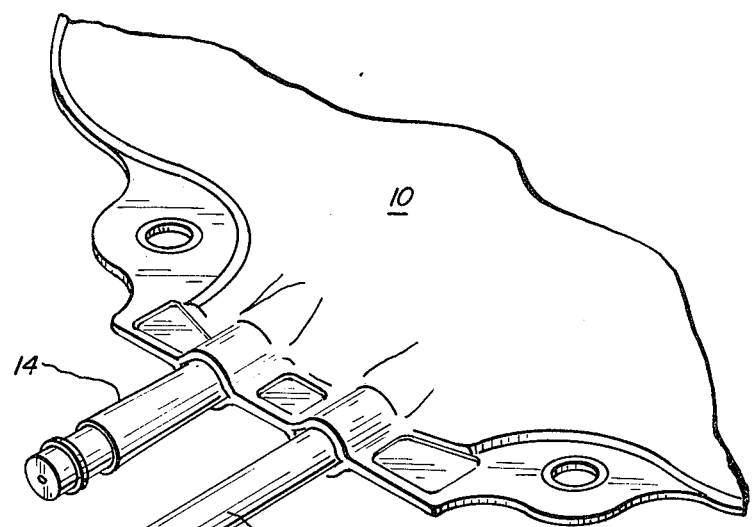
FIG. 2
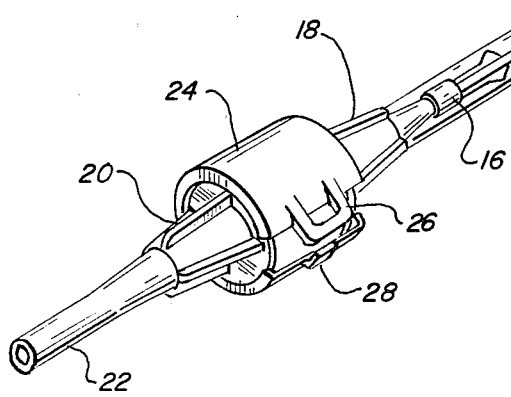
FIG. 1
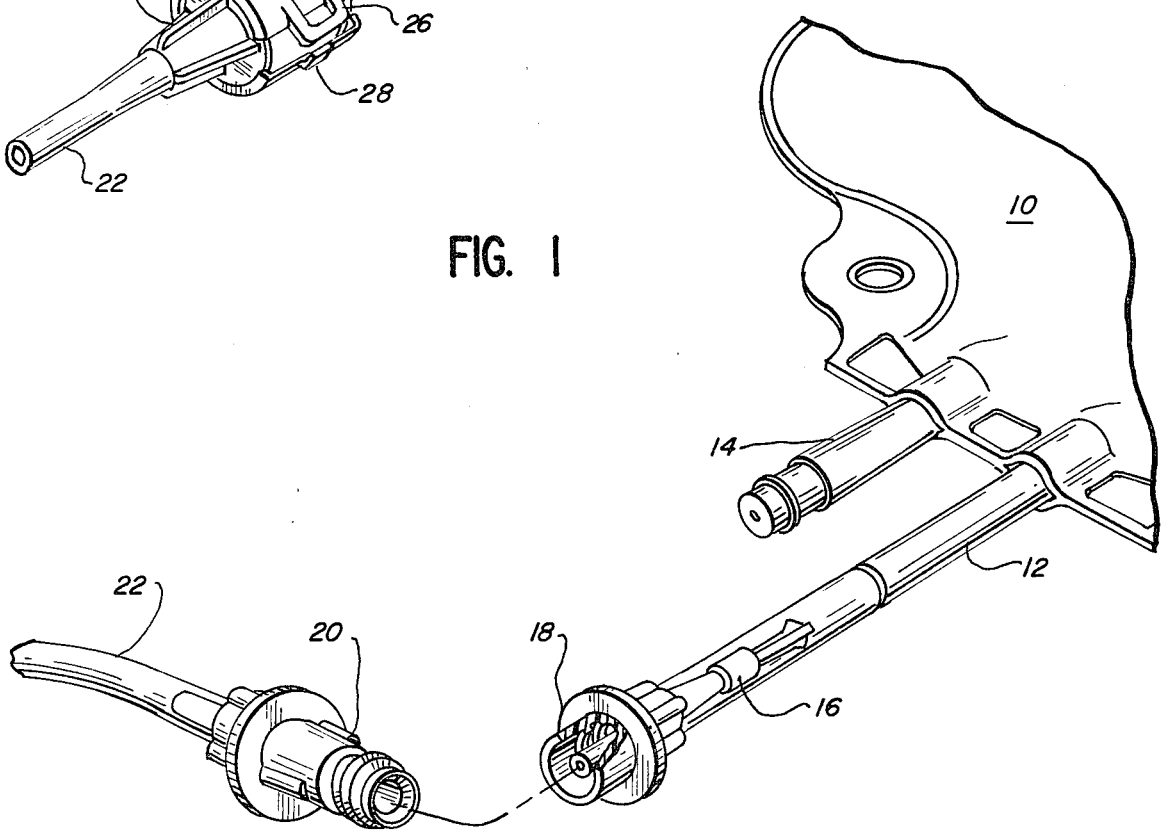

FIG. 5
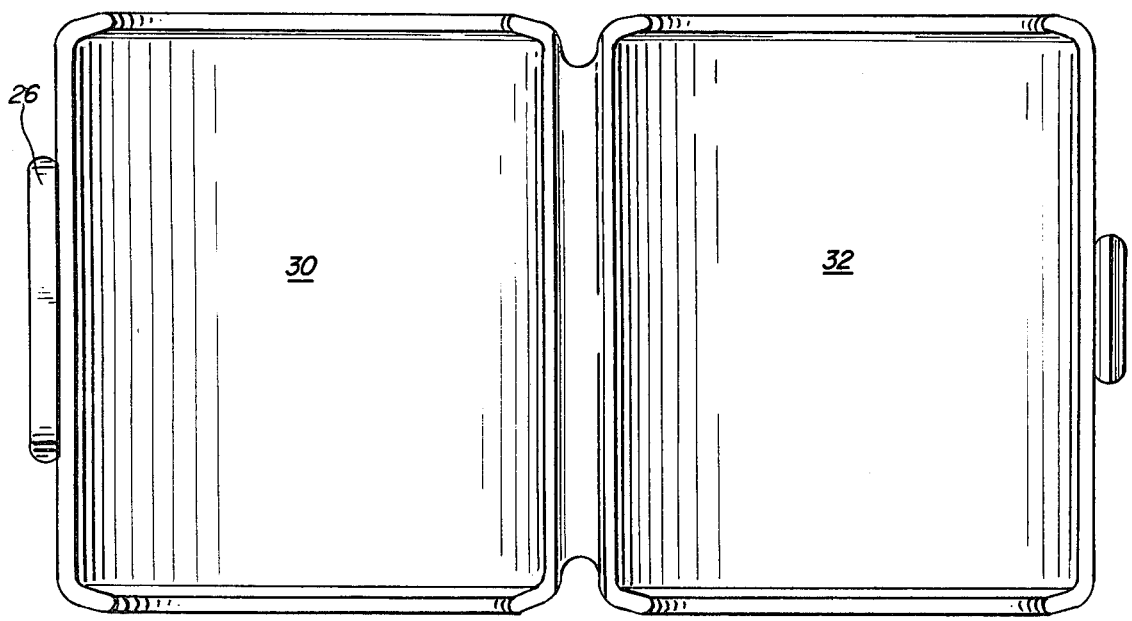
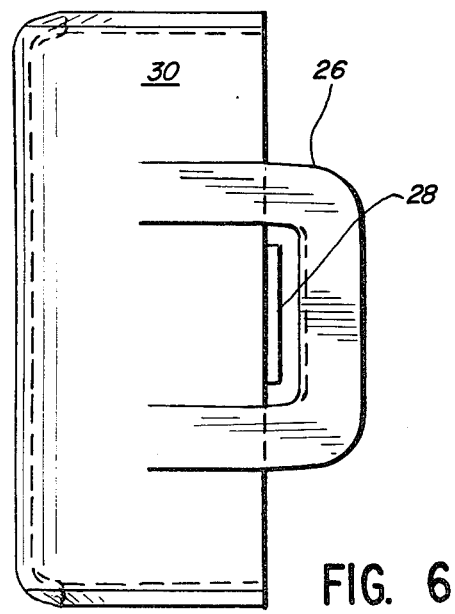
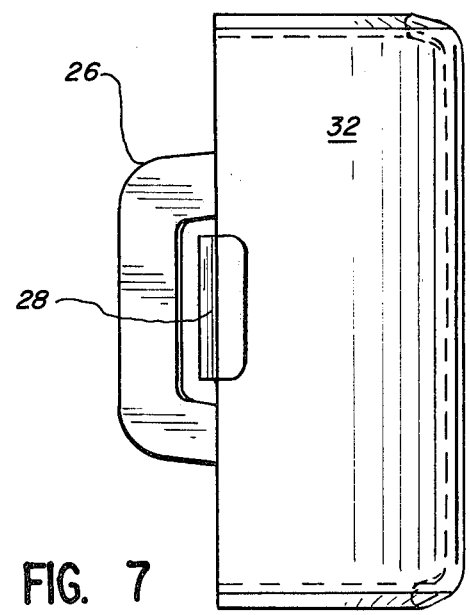
FIG. 6　　FIG. 7

CONNECTION SITE PROTECTOR

BACKGROUND OF THE INVENTION

This invention relates to a protector, primarily for use in medical applications. Its principal contemplated use is to surround and protect from contamination any connection site used by a patient in practicing a technique of kidney dialysis known as continuous ambulatory peritoneal dialysis.

Currently, the most widely used method of kidney dialysis for treatment of End Stage Renal Disease (ESRD) is "hemodialysis." Here, the patient's blood is cleansed by passing it through an artificial kidney in a kidney dialysis machine. By the process of diffusion across a semipermeable membrane in the artificial kidney, impurities and toxins are removed from the patient's blood to thereby perform a function of the patient's natural kidneys. Hemodialysis is required several times a week, each dialysis requiring several hours in a dialysis center or at home. During dialysis, the patient is "tied" to the machine by venous and arterial blood lines which convey his blood to and from the artificial kidney.

Although used less frequently than hemodialysis, a procedure known as "intermittent peritoneal dialysis" is an accepted method for treating ESRD. In this procedure, a dialysis solution is infused into the patient's peritoneal cavity by means of tubing and a catheter. The peritoneum, which defines the peritoneal cavity, contains many small blood vessels and capillary beds which act as a natural semipermeable membrane. This natural membrane may be contrasted with the artificial membrane used in hemodialysis. In both cases, however, impurities and toxins in the blood are removed by diffusion across a membrane—a cellulose membrane of an artificial kidney or a peritoneal membrane of a peritoneal cavity.

In intermittent peritoneal dialysis, dialysis solution remains in the patient's peritoneal cavity for a time sufficient for blood impurities to be removed by diffusion across the peritoneal membrane into the dialysis solution. The impurity containing dialysis solution then is drained from the peritoneal cavity by means of the catheter and tubing, and a fresh supply of dialysis solution is infused. Intermittent peritoneal dialysis utilizes pumps or other auxiliary equipment to which the patient is "tied" during dialysis; here also the patient must remain sedentary.

Continuous ambulatory peritoneal dialysis is another type of peritoneal dialysis which uses the peritoneum as a semipermeable membrane. This procedure has the important advantage, however, of enabling the patient to be ambulatory and conduct a normal routine during dialysis. The patient is not "tied" to a machine and he must be sedentary only for the time period required to drain and infuse dialysis solution from and into the peritoneal cavity. This infusion and draining is handled by tubing and a surgically implanted, indwelling catheter in the patient's abdominal wall and in communication with his peritoneal cavity.

The continuous ambulatory peritoneal dialysis procedure is intended to be a patient self-care technique once the catheter is surgically implanted. Thus, it is important that the apparatus involved, e.g., tubing solution container, and connections be simple and easy to use. The present invention is designed to be a simple and effective means of protecting any connection site between a patient's implanted catheter and a solution container of dialysis solution. The invention concerns a protector which surrounds and protects from contamination a connection site for use by a patient practicing continuous ambulatory peritoneal dialysis. This protector can be used, however, with a variety of medical devices which would fit within the protector.

Devices have been used in the past to secure and protect the connecting site of two ends of an external shunt typically implanted in the forearm of a patient being treated for kidney disease by hemodialysis. These devices were similar in design to the present invention, but did not include a material capable of holding a sterilizing agent in the device and in contact with the connection site.

With the advent of dialysis solution contained in plastic bags, and the development of continuous ambulatory peritoneal dialysis, it is desirable to have a simple contamination protector for use by patients to protect any connection site between a patient's tubing and a solution container. Typically, the connection site between the patient's indwelling catheter and the tubing through which dialysis solution flows is made by trained medical personnel in a clinical environment, and the tubing is not changed more frequently than once a month. However, at the distal end of the tubing, the patient connects and disconnects a dialysis solution container approximately four times per day. To prevent infection, it is extremely important that these connections be made in as aseptic a manner as possible and that the connection site remain free of debris and bacterial contamination. A simple effective contamination protector which would surround the connection site would be important, particularly from a patient self-care standpoint, when practicing continuous ambulatory peritoneal dialysis. It is, therefore an object of this invention to provide a contamination protector for connection sites in continuous ambulatory peritoneal dialysis, which is easy to open and close and is effective in preventing debris and bacterial contamination from entering the tubing at the connection site.

The protector of this invention comprises two halves which operate much like a "clamshell". The protector in the open position is placed around the connection site, the halves are swung to a closed position surrounding and in contact with the connection site, and secured in that position by a closure means. A gauze pad or other material soaked with an antibacterial agent such as povidone-iodine is first wrapped around the connection site by the patient and then secured in place by the protector. Alternatively, the protector can have integral with it a sponge or other like material impregnated with an antibacterial agent. In this embodiment, the antibacterial sponge remains with the protector and surrounds the connection site as the protector is closed.

Ease of operation of the protector is important since continuous ambulatory peritoneal dialysis is primarily a patient self-care technique, and because a large number of patients who practice continuous ambulatory peritoneal dialysis have limited physical capacity because of poor eyesight, weakness, arthritis and the like. This invention is also advantageous for use by children and geriatric patients.

SUMMARY OF THE INVENTION

The protector of the present invention is generally cylindrical in shape, and can be manually manipulated to an open or closed position. In the closed position the protector is hollow and open at each end. It comprises at least two hinged and generally semicircular protector segments.

The segments are hinged so that they can be opened and closed. The inner surface of each segment carries a material, typically a gauze pad or sponge, which is capable of holding a sterilizing agent such as povidone-iodine. The gauze or sponge material is secured by the protector around the connection site offering substantial protection from bacterial contamination. Alternatively, a gauze pad, soaked with antiseptic, can first be wrapped around the connection site and the protector "clamshell" casing can then be closed over the pad.

BRIEF DESCRIPTION OF THE DRAWINGS

Other objects, features and advantages of the present invention will become more fully apparent from the following detailed description of the preferred embodiment, the appended claims and the accompanying drawings in which:

FIG. 1 is a perspective view, with portions broken away, of a plastic solution container with male connector extending from a port of the solution container about to be mated with a female connector at the distal end of the tubing attached to a patient's catheter;

FIG. 2 is a perspective view, with portions broken away, of a plastic solution container with the male connector part of FIG. 1 shown mated with the female connector part of FIG. 1 and the protector of this invention shown in a closed position around the connection site between the male and female connector;

FIG. 5 is an enlarged top view of the protector shown in the open position;

FIG. 6 is an enlarged end view with the protector shown in the open position;

FIG. 7 is an enlarged end view of the other end of the protector shown in the open position.

DETAILED DESCRIPTION OF THE PREFERRED EMBODIMENT

Figure 3:
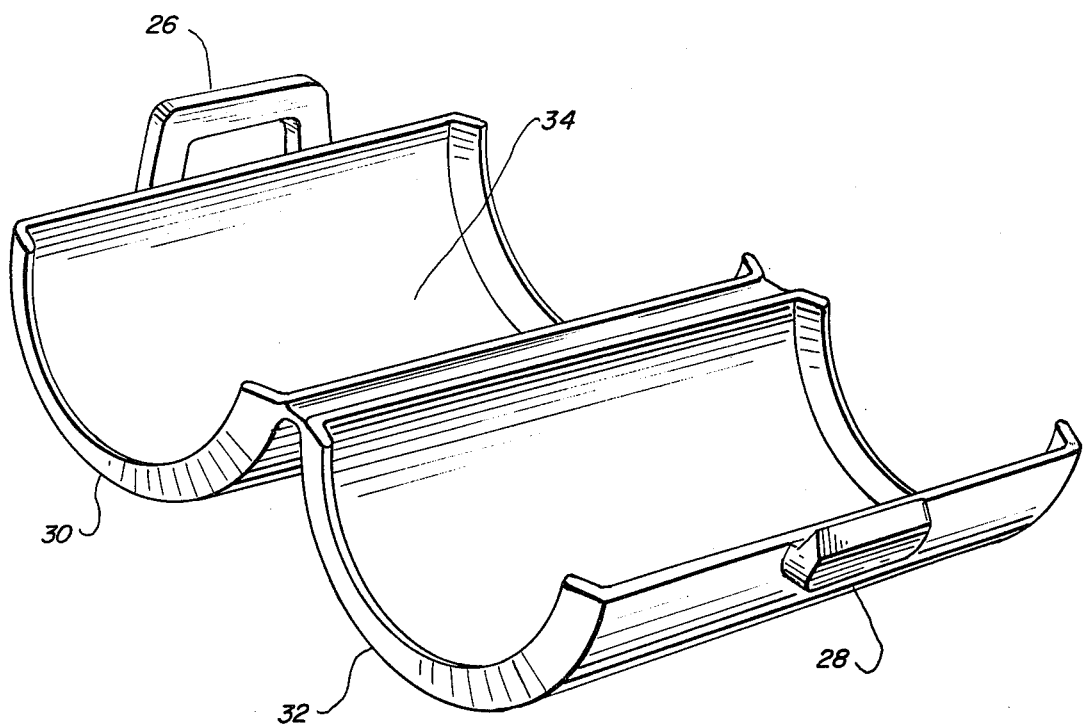
FIG. 3 is an enlarged perspective view of the protector shown in an open position without absorbent material capable of holding a sterilizing agent carried by the inner wall of the invention.

The preferred embodiment of the protector of this invention is illustrated by way of example in FIGS. 2–7. FIG. 1 shows a plastic dialysis solution container with a male connector extending from a port about to be mated with a female connector which is at the distal end of the tubing of a patient practicing continuous ambulatory peritoneal dialysis.

Referring to FIG. 1, a peritoneal dialysis solution container 10 is shown with a tubular outlet port 12 and a tubular medication injection port 14; both ports are in communication with the inside of the solution container 10. A frangible valve 16 is shown in outlet port 12. The frangible valve, when broken, enables solution to flow from dialysis solution container 10. A male connector 18 is shown with portions broken away for clarity at the distal end of tubular portion 12. Female connector 20 is carried at the distal end of patient tubing 22.

Referring to FIG. 2, the dialysis solution container and connectors are shown in the connected position with the present invention shown as 24 surrounding and protecting the connection site between male connector 18 and female connector 20; latch 26 is shown about to be mated with tab 28 thereby securing the present invention in a closed position. The invention has a general "clamshell" configuration.

Referring to FIG. 3, the protector is shown to be generally cylindrical in shape and comprising hinged and generally semicircular segments 30 and 32. Inner wall 34 of each segment is adapted to carry a material capable of holding a sterilizing agent. When the protector is closed with a material inside it capable of holding a sterilizing agent, the sterilizing agent will be held firmly in contact with the connection site and prevent bacterial contamination of the site. The protector is secured in a closed position by means of latch 26 mating with tab 28. It will be readily apparent that other means of closing the protector could be used.

Figure 4:
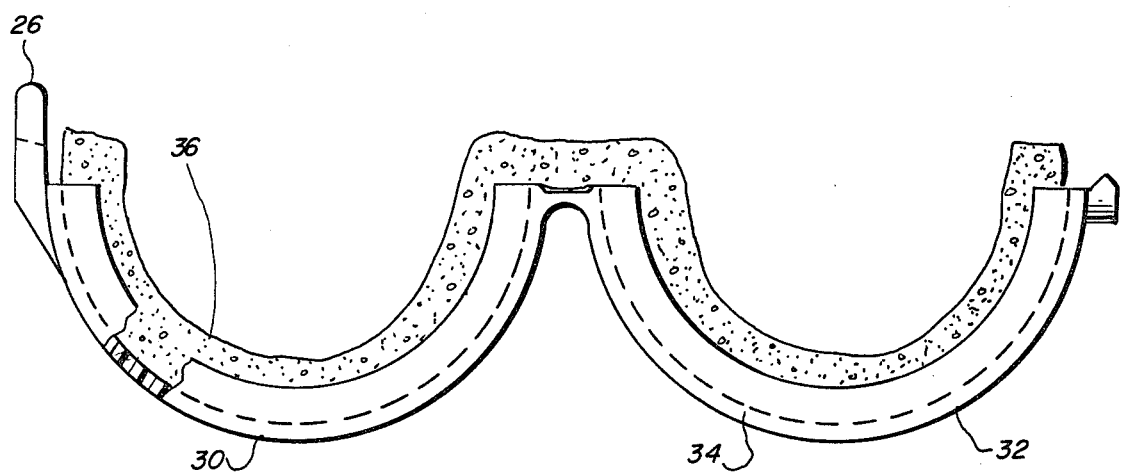
FIG. 4 is an enlarged front view of the protector shown in the open position with material capable of holding a sterilizing agent carried by the inner wall.

Referring to FIG. 4, the inner wall 34 of the invention is shown carrying a material 36 which is capable of holding a sterilizing agent. The material 36 is preferably gauze or a sponge material which will effectively holding a sterilizing agent, and when the invention is closed around a connection site, the sterilizing agent will intimately contact the connection site and protect it from bacterial contamination.

This invention can be used in at least two ways. A gauze pad can be folded and wrapped around the connection site prior to closing the protector around the connection site, or alternatively, a sponge or other like material can be made integral with inner wall 34 of the protector and remain permanently with it. In this latter embodiment the supply of sterilizing agent would be replenished from time to time, or the sterilizing agent could be applied during manufacture of the protector and the protector used by the patient only one time.

A patient would use the protector with integral material in the following manner. First, he makes the connection between the dialysis solution container and a tubing set connected to the patient's catheter. Next a gauze or sponge material which is carried by and integral with the inner surface of the protector is soaked with an antiseptic, typically a povidone-iodine solution, or the solution can be preapplied during manufacture of the protector. Finally, the protector is closed and secured around the connection site thereby protecting the site from debris and bacterial contamination. The protector is removed when the connection is to be broken in preparation for connecting a fresh dialysis solution container. If the protector with integral sponge or gauze material is reused, fresh antiseptic solution is added to the material each time a connection site is covered, or it is possible that the material could be impregnated with a "dry" sterilizing agent that would not require replenishment each time the protector would be used to protect a new connection site.

If the protector does not integrally carry a material, an antiseptic gauze or like pad can be first wrapped around the connection site. Then, the protector can be closed around the pad. The pad is changed each time a connection is made, but the protector can be reusable.

While the present invention has been disclosed in connection with the preferred embodiment thereof and an alternative embodiment thereof, it should be understood that there may be other embodiments, which fall within the sphere and scope of this invention as defined by the following claims.

What is claimed is:

1. The combination of a connection site in contact with and covered by a material containing a sterilizing agent, and a manually openable and closable protector of generally cylindrical shape;

said protector being hollow and open at each end when in the closed position;

said protector comprising at least two hinged and generally semicircular segments, the inner wall of said segments adapted to surround and protect from contamination the covered connection site when said protector is in a closed position and surrounding said material containing a sterilizing agent.

2. The combination of a connection site in contact with and covered by a material containing a sterilizing agent, and a manually openable and closable protector, said protector being hollow and open at each end when in the closed position, said protector comprising at least two hinged segments, the inner wall of said segments being adapted to surround and protect from contamination the covered connection site when said protector is in a closed position and surrounding said material containing a sterilizing agent.

* * * * *

REEXAMINATION CERTIFICATE (369th)

United States Patent [19]

Dennehey et al.

[11] B1 4,340,052

[45] Certificate Issued Jul. 16, 1985

[54] CONNECTION SITE PROTECTOR

[75] Inventors: T. Michael Dennehey, Arlington Heights; Richard J. Greff, Ingleside; Ludwig Wolf, Jr., Crystal Lake, all of Ill.

[73] Assignee: Baxter Travenol Laboratories, Inc., Deerfield, Ill.

Reexamination Request:
No. 90/000,580, Jun. 25, 1984

Reexamination Certificate for:
Patent No.: 4,340,052
Issued: Jul. 20, 1982
Appl. No.: 194,733
Filed: Oct. 7, 1980

[51] Int. Cl.³ .............................................. A61M 3/00
[52] U.S. Cl. .................................................. 604/283
[58] Field of Search ............... 604/905, 239, 240, 241, 604/242, 243, 264, 265, 197, 199, 86, 192; 285/260

[56] References Cited

U.S. PATENT DOCUMENTS

| | | | |
|---|---|---|---|
| 2,857,912 | 10/1958 | Feinstone et al. | 604/86 |
| 3,456,965 | 7/1969 | Gajewski et al. | 285/260 |
| 3,976,311 | 8/1976 | Spendlove | 285/12 |
| 4,043,333 | 8/1977 | Munsch | 604/192 |
| 4,354,490 | 10/1982 | Rogers | 128/213 |

FOREIGN PATENT DOCUMENTS

2853635  6/1980  Fed. Rep. of Germany .

OTHER PUBLICATIONS

Proceedings of an International Symposium at Paris, Nov. 2, 3, 1979, "Continuous Ambulatory Peritoneal Dialysis", *Excerpta Medica* 1980.

"Going Home With Confidence", A Travenol publication (1979).

*Primary Examiner*—John D. Yasko

[57] ABSTRACT

A contamination protector for a medical device, principally for use in surrounding and protecting a connection between a plastic dialysis solution container (10) and tubing (22) carried by a patient practicing continuous ambulatory peritoneal dialysis. The protector is generally cylindrical in shape, and opens and closes much like a "clamshell." The inner wall surface (34) of the protector is adapted to carry a material (36) which holds a sterilizing agent in contact with a medical connection when the protector is in the closed position.

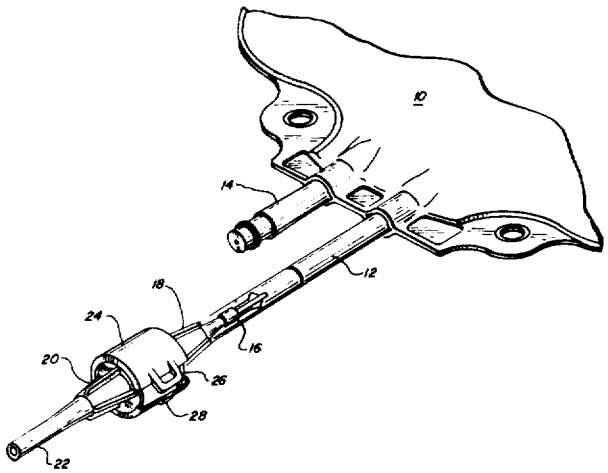

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1 and 2 are cancelled.

* * * * *